United States Patent [19]

Engel et al.

[11] Patent Number: 4,555,521
[45] Date of Patent: Nov. 26, 1985

[54] NEMATICIDAL 3-SUBSTITUTED-4-PHENYL-1,2,5-THIADIAZOLES

[75] Inventors: John F. Engel, Washington Crossing; Joseph M. Puglis, Newtown, both of Pa.

[73] Assignee: FMC Corporation, Philadelphia, Pa.

[21] Appl. No.: 552,595

[22] Filed: Nov. 16, 1983

[51] Int. Cl.⁴ .................... C07D 285/10; A01N 43/82
[52] U.S. Cl. .................................... 514/362; 548/134; 548/135
[58] Field of Search ................. 548/134, 135; 424/269

[56] References Cited

U.S. PATENT DOCUMENTS

| | | | |
|---|---|---|---|
| 3,391,152 | 7/1968 | Weinstock | 548/134 |
| 3,484,452 | 12/1964 | Tull | 548/135 |
| 4,145,550 | 3/1979 | Belanger | 544/367 |

OTHER PUBLICATIONS

Weinstock et al., J. Org. Chem. 32, 2823 (1967).
Masuda et al., J. Chem. Soc. Perkins I, 1033 (1981).

*Primary Examiner*—Robert Gersil
*Attorney, Agent, or Firm*—Robert L. Andersen; H. Robinson Ertelt

[57] ABSTRACT

A method for controlling nematodes in agricultural crops utilizing selected 3-substituted-4-phenyl-1,2,5-thiadiazoles, nematicidal compositions thereof, and novel compounds useful therefor are disclosed and exemplified.

6 Claims, No Drawings

NEMATICIDAL 3-SUBSTITUTED-4-PHENYL-1,2,5-THIADIAZOLES

The present invention is directed to a method for control of nematodes which adversely affect agricultural crops, to nematicidal compositions, and to novel 3-substituted-4-phenyl-1,2,5-thiadiazoles useful in the control of nematodes.

In a first aspect of this invention there is provided a method for controlling nematodes which comprises applying to the soil in which plants are or are to be planted a nematicidal amount of a compound of the formula

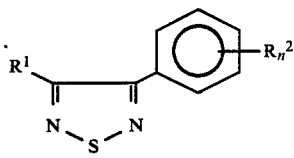

in which:
(a) $R^1$ is halogen, $R^2$ is halogen, cyano, methyl, methoxy, halomethoxy, or 4-methylcarbonyloxy, and n is 0 or 1; or $R^2$ is halogen and n is 2; or
(b) $R^1$ is methoxy, $R^2$ is halogen, cyano, 4-methyl or 4-methoxy, and n is 0 or 1; or
(c) $R^1$ is halomethoxy, $R^2$ is halogen, and n is 1; or
(d) $R^1$ is dimethylaminocarbonyloxy or dimethylaminocarbonylthio, $R^2$ is halogen or methyl, and n is 0 or 1; or
(e) $R^1$ is cyano, methylthio, 2-propenyloxy, 2-propynyloxy, 2,2,2-trifluoroethoxy, or phenoxy, and n is 0.

In another aspect of this invention there are provided a nematicidal composition which comprises a nematode controlling amount of the compounds described above in admixture with an agriculturally acceptable vehicle.

In a third aspect of the invention there are provided novel compounds of formula I in which:
(a) $R^1$ is halogen, $R^2$ is halogen, cyano, methyl, methoxy, halomethoxy, or 4-methylcarbonyloxy, and n is 1; or $R^2$ is halogen and n is 2; or
(b) $R^1$ is methoxy, $R^2$ is halogen, cyano, 4-methyl or 4-methoxy and n is 1; or
(c) $R^1$ is halomethoxy, $R^2$ is halogen, and n is 1; or
(d) $R^1$ is dimethylaminocarbonyloxy or dimethylaminocarbonylthio, $R^2$ is halogen or methyl, and n is 0 or 1; or
(e) $R^1$ is cyano, methylthio, 2-propenyloxy, 2-propynyloxy, 2,2,2-trifluoroethoxy, or phenoxy, and n is 0.

The compounds set forth in Table I further illustrate the nematicidal compounds for use in accordance with this invention.

The following examples illustrate preparation of the compounds described above.

EXAMPLE 1

3-Chloro-4-(3-chlorophenyl)-1,2,5-thiadiazole

Step A alpha-Amino-(3-chlorophenyl)acetonitrile

By the method of R. Crosley and A. Curron, J. C. S. Perkin I, 20, 2327 (1974), incorporated herein by reference, 18.5 g (0.178 mole) of sodium bisulfite, 200 ml of water, 25.0 g (0.178 mole) of 3-chlorobenzaldehyde and 30 ml of concentrated ammonium hydroxide were reacted to produce 3.3 g of alpha–amino(3-chlorophenyl)acetonitrile (m.p. 31°-33° C.).

Step B 3-Chloro-4-(3-chlorophenyl)-1,2,5-thiadiazole

In a manner analogous to that of L. Weinstock, et al., J. O. C., 32, 2823 (1967), incorporated herein by reference, 2.5 g (0.015 mole) of alpha-amino-(3-chlorophenyl)acetonitrile was reacted with 6.07 g (0.045 mole) of sulfur monochloride in 15 ml of N,N-dimethylformamide to produce 3.05 g of 3-chloro-4-(3-chlorophenyl)-1,2,5-thiadiazole, Compound 2 of Table I.

EXAMPLE 2

3-Chloro-4-(3-methoxyphenyl)-1,2,5-thiadiazole

Step A alpha-Amino(3-methoxyphenyl)acetonitrile hydrochloride

By the method of R. Steiger, Org. Syn. Coll. Vol. 3, pg 84-86, incorporated herein by reference, 16.7 g (0.34 mole) of sodium cyanide and 19.4 g (0.36 mole) of ammonium chloride in 80 ml of water were reacted with 45.0 g (0.33 mole) of m-anisaldehyde in 70 ml of methanol. Subsequent treatment with gaseous hydrogen chloride produced 31.5 g of alpha-amino-(3-methoxophenyl)acetonitrile hydrochloride (m.p. 165°-167° C. dec.).

Step B 3-Chloro-4-(3-methoxyphenyl)-1,2,5-thiadiazole

In a manner analogous to that of L. Weinstock, et al., supra, 5.0 g (0.025 mole) of alpha-amino-(3-methoxyphenyl)acetonitrile hydrochloride and 10.16 g (0.0753 mole) of sulfur monochloride in 20 ml of N,N-dimethylformamide were reacted to produce 2.3 g of 3-chloro-4-(3-methoxyphenyl)-1,2,5-thiadiazole as an oil, Compound 12 of Table I. Compounds 1, 3–7, 9–11, 13, 16, and 17 of Table I were also prepared by this method.

EXAMPLE 3

3-Fluoro-4-(3-methoxyphenyl)-1,2,5-thiadiazole

By the method of M. Geisel and R. Mews (Chem. Ber. 115, 2135 (1982), incorporated herein by reference, 2.0 g (0.0088 mole) of 3-chloro-4-(3-methoxyphenyl)-1,2,5-thiadiazole (from Example 2) was heated with 2.04 g (0.035 mole) of potassium fluoride in 20 ml of sulfolane at 180° C. to produce 0.48 g of 3-fluoro-4-(3-methoxyphenyl)-1,2,5-thiadiazole, Compound 21 of Table I. Compounds 18–20 of Table I were also prepared by this method.

EXAMPLE 4

4-(4-Acetylphenyl)-3-chloro-1,2,5-thiadiazole

Step A 3-Chloro-4-(4-hydroxyphenyl)-1,2,5-thiadiazole

By the method described in 'Advanced Organic Synthesis, Methods and Techniques' Academic Press, p 66 (1971), incorporated herein by reference, 2.0 g (0.0088 mole) of 3-chloro-(4-methoxy-phenyl)-1,2,5-thiadiazole (prepared in manner of Example 2) was reacted with 11.0 g (0.044 mole) of boron tribromide in 60 ml of methylene chloride to produce 1.63 g of 3-chloro-4-(4-hydroxyphenyl)-1,2,5-thiadiazole (m.p. 135°-136.5° C.).

Step B 4-(4-Acetylphenyl)-3-chloro-1,2,5-thiadiazole

Acylation of 0.5 g (0.0024 mole) of 3-chloro-4-(4-hydroxyphenyl)-1,2,5-thiadiazole with 0.2 g (0.0026 mole) of acetyl chloride and 0.36 g (0.0026 mole) of potassium carbonate in 15 ml of N,N-dimethylformamide produced 0.22 g of 4-(4-acetylphenyl)-3-chloro-1,2,5-thiadiazole, Compound 15 of Table I.

EXAMPLE 5

4-(4-Chlorophenyl)-3-methoxy-1,2,5-thiadiazole

Step A Ethyl alpha-bromo-(4-chlorophenyl)acetate

By the method of E. Schwenk and D. Papa, J. A. C. S. 70, 3626 (1948), incorporated herein by reference, 86.8 g (0.509 mole) of p-chlorophenylacetic acid was treated with 100 ml of thionyl chloride. Subsequent reaction with 83.2 g (0.52 mole) of bromine followed by 100 ml of ethanol produced 78.9 g of ethyl alphabromo-(4-chlorophenyl)acetate as an oil.

Step B alpha-Amino-(4-chlorophenyl)acetamide hydrobromide

By the method of T. Naito, et al., Chem. Pharm. Bull. 16, 544 (1968), incorporated herein by reference, 50.0 g (0.18 mole) of ethyl alpha-bromo-(4-chlorophenyl)acetate, 110 ml of concentrated ammonium hydroxide solution, and ammonia gas in 125 ml of ethanol were reacted to produce 20.0 g of alpha-amino(4-chlorophenyl)acetamide hydrobromide (m.p. 273°–280° C. dec.).

Step C 4-(4-Chlorophenyl)-3-hydroxy-1,2,5-thiadiazole

Alpha-amino-(4-chlorophenyl)acetamide hydrobromide, 5.0 g (0.019 mole) was then reacted with 7.61 g (0.056 mole) of sulfur monochloride in 20 ml of N,N-dimethylformamide to produce 2.0 g of 4-(4-chlorophenyl)-3-hydroxy-1,2,5-thiadiazole (m.p. 240°–242° C.).

Step D 4-(4-Chlorophenyl)-3-methoxy-1,2,5-thiadiazole

By the method of L. Weinstock, et al., supra, 0.5 g (0.0023 mole) 4-(4-chlorophenyl)-3-hydroxy-1,2,5-thiadiazole, 0.36 g (0.0026 mole) of potassium carbonate and 0.37 g (0.0026 mole) of iodomethane in 15 ml of N,N-dimethylformamide were reacted to produce 0.45 g of 4-(4-chlorophenyl)-3-methoxy-1,2,5-thiadiazole, Compound 25 of Table I. Compounds 22–24, 26–29, 31, 35, 37, and 39–41 were also prepared by this method, except that, in some cases sodium carbonate was used in place of potassium carbonate and/or an appropriate bromide or chloride was used in place of methyl iodide.

EXAMPLE 6

4-(4-Cyanophenyl)-3-methoxy-1,2,5-thiadiazole

In a manner similar to L. Friedman and H. Shechter, J.O.C., 26, 2522 (1961), incorporated herein by reference, 1.15 g (0.0043 mole) of 4-(4-bromophenyl)-3-methoxy-1,2,5-thiadiazole, 0.46 g (0.0051 mole) of copper cyanide, 15 ml of N,N-dimethylformamide, and a solution of 66.5 g of sodium cyanide in 200 ml of water were reacted to produce 0.58 g of 4-(4-cyanophenyl)-3-methoxy-1,2,5-thiadiazole, Compound 30 of Table I. Compounds 8 and 44 were also prepared by this method.

EXAMPLE 7

3-Phenoxy-4-phenyl-1,2,5-thiadiazole

Under a dry nitrogen atmosphere 4.1 g (0.0021 mole) of 3-chloro-4-phenyl-1,2,5-thiadiazole was added to a stirred mixture of 3.73 g (0.0027 mole) of potassium carbonate and 2.4 g (0.0026 mole) of phenol in 50 ml of N,N-dimethylformamide. After complete addition the mixture was heated at 120° C. for 21 hours. The mixture was cooled, poured into 400 ml of ice water and the mixture extracted with diethyl ether. The extract was dried over anhydrous magnesium sulfate and filtered. The filtrate was evaporated under reduced pressure to leave a residue. The residue was purified by column chromatography on silica gel, eluted with n-hexane:methylene chloride (1:1) to yield 4.8 g of 3-phenoxy-4-phenyl-1,2,5-thiadiazole, Compound 38 of Table I.

EXAMPLE 8

3-Methoxy-4-(4-methoxyphenyl)-1,2,5-thiadiazole

Under a dry nitrogen atmosphere 3.0 g (0.0013 mole) of 3-chloro-4-(4-methoxyphenyl)-1,2,5-thiadiazole (prepared by the method of Example 2 from p-anisaldehyde) was added to a stirred suspension of 0.78 g (0.0015 mole) of anhydrous sodium methoxide in 30 ml of N,N-dimethylformamide. The reaction mixture became exothermic. The mixture was allowed to cool slowly to room temperature and stir for approximately 18 hours. Approximately 0.1 g of anhydrous sodium methoxide was added and the mixture stirred an additional three hours. The reaction mixture was poured into 250 ml of ice water and the total extracted with diethyl ether. The ether extract was washed with water, dried over anhydrous magnesium sulfate and filtered. The solvent was evaporated from the filtrate under reduced pressure to leave a beige solid. The solid was chromatographed on silica gel, eluted with methylene chloride to give a yellow solid. The yellow solid was purified by column chromatography on silica gel, eluted with n-hexane:ethyl acetate (7:1) to yield 0.7 g of 3-methoxy-4-(4-methoxyphenyl)-1,2,5-thiadiazole, Compound 32 of Table I.

The nematicides of this invention, like most agricultural chemicals, are generally not applied full strength, but are formulated with agriculturally acceptable carriers normally employed for facilitating the dispersion of active ingredients, various additives, and optionally with other active ingredients, recognizing that the formulation and mode of application of a toxicant may affect the activity of the material. The present compounds may be applied, for example, as powders or liquids, the choice of application varying with the nematode species and environmental factors present at the particular locus of infestation. Thus, the compounds may be formulated as granules, as dusts, as wettable powders, as emulsifiable concentrates, as solutions, as dispersions, as controlled release compositions, and the like.

A typical formulation may vary widely in concentration of the active ingredient depending on the particular agent used, the additives, carriers, or other active ingredients used, and the desired mode of application. With due consideration to these factors, the active ingredient of a typical formulation may, for example, be suitably present at a concentration of from about 0.5% up to about 99.5% by weight of the formulation. Substantially inactive ingredients such as adjuvants, diluents, and carriers may comprise from about 99.5% by weight to as low as about 0.5% by weight of the formulation. Surface active agents, if employed in the formulation, may be present at various concentrations, suitably in the range of 1 to 30% by weight. Provided below is a general description of exemplary types of formulations which may be employed for dispersion of the nematicides of the present invention.

Dusts are admixtures of the active ingredient with finely divided solid carriers and/or diluents such as talc, natural clays, kieselguhr, pyrophyllite, chalk, diatomaceous earths, calcium phosphates, calcium and magnesium carbonates, sulfur, lime, flours, and other organic and inorganic solid carriers. These finely divided formulations generally have an average particle size of less than about 50 microns (325 mesh, Standard U.S. Sieve Series). In most cases, the active ingredient will be present in dust formulations at a concentration in the range of 1 to 15%, and occasionally from 1% to about 30%, the balance of the composition typically comprising one or more agriculturally acceptable inerts as adjuvant, carrier, or diluent.

Wettable powders, also useful formulations for these nematicides, are in the form of finely divided particles which disperse readily in water or other liquid vehicles. The wettable powder is ultimately applied as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (mp less than 100° C.) are suitably formulated in the concentration range of 5 to 50% by weight; usually 10 to 30%; high melting solids (mp greater than 100° C.) being formulated in the range of 5 to 95% by weight, usually 50 to 85%. An agriculturally acceptable carrier or diluent, frequently including a small amount of a surfactant to facilitate wetting dispersion and suspension, accounts for the balance of the formulation.

Microencapsulated or other controlled release formulations may also be used with nematicides of this invention for control of nematodes.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application of the nematicide, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5% to 5% being surfactant and liquid carrier.

Flowables are similar to EC's except that the ingredient is suspended in a liquid carrier, generally water. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in nematicidal formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of lone-chain mercaptans and ethylene oxide. Many other types of useful surface-active agents are available in commerce. The surface-active agent, when used, normally comprises from 1 to 15% by weight of the nematicidal composition.

Other useful formulations include simple solutions of the active ingredient in a relatively non-volatile solvent such as corn oil, kerosene, propylene glycol, or other organic solvents. This type of formulation is particularly useful for ultra low volume application.

The concentration of the nematicide in use dilution is normally in the range of about 2% to about 0.1%. Many variations of spraying, dusting, and controlled or slow release compositions in the art may be used by substituting or adding a compound of this invention into compositions known or apparent to the art.

Nematicidal compositions may be formulated and applied with other suitable active ingredients, including other nematicides, insecticides, acaricides, fungicides, plant regulators, herbicides, fertilizers, etc.

In applying the foregoing chemicals, an effective nematode controlling amount of active ingredient must be applied, sometimes referred to herein as a nematicidal amount. While the application rate will vary widely depending on the choice of compound, the formulation and mode of application, the plant species being protected and the planting density, a suitable use rate may be in the range of 0.5 to 25 kg/hectare, preferably 1 to about 20 kg/hectare.

The compounds of this invention are usually applied by incorporating a formulation thereof into the soil in which agricultural crops are or are to be planted, i.e., the locus of infestation. Some of the compounds are active at the locus of infestation when applied to the above ground portions of the plant and may be so applied.

The following are specific examples of formulations which may be utilized in accordance with the present invention:

| A typical 5% dust (wt/wt) formulation is as follows: | |
|---|---|
| Test Compound | 5% |
| Base | 95% |
| 96% Attaclay | |
| 2% highly purified sodium lignosulfonate (100%) | |
| 2% powdered sodium alkylnaphthalene sulfonate (75%) | |
| A typical Attaclay granular formulation is as follows: | |
| Test Compound | 5% |
| Attaclay | 95% |
| A typical sand core granule formulation is as follows: | |
| 75% base | 6.64% |
| Test Compound | 75% |
| Sodium alkylnaphthalenesulfonate | 1% |
| Sugar-free sodium based sulfonate of Kraft lignin | 4% |
| Barden clay | 20% |
| Polyvinyl acetate | 0.75% |
| Water | 1.00% |
| Silica (20/40 mesh) | 91.61% |

The Attaclay granular formulation may be prepared by dissolving the active ingredient in a volatile solvent such as methylene chloride, then coating the attaclay with the resulting solution or by other methods well known to those skilled in the art, and allowing the solvent to evaporate. The sand core granule may be prepared by incorporating the active ingredient into a suitable base, then applying to sand to form a coated granule generally utilizing a sticker such as polyvinyl acetate.

The compounds of this invention were tested for biological activity as formulations of the active ingredient as an acetone solution, as a dust formulation, or as a granular formulation. The activity against root-knot nematode (Meloidogyne incognita) was determined by incorporating the compound of the invention in nematode infested soil at rates in the range of 25 ppm to 1.25 ppm. Several tomato plants were planted in the nematode infested soil. Two weeks after planting the tests were evaluated to ascertain the degree of galling on the roots of the plant, indicating the control provided by the test chemical.

The results, expressed as "knot index", are set forth in Table II. Knot index is a numerical designation assigned at evaluation, having the following meanings:

| Knot Index | Observed Degree of Control |
|---|---|
| 0 | No swellings - complete control |
| 1 | 75% less swellings than control plants |
| 2 | 50% less swellings than control plants |
| 3 | 25% less swellings than control plants |
| 4 | About same as control plants - no control |

When the Knot Index is between 0 and 1 it is further sub-divided as follows to indicate how close the degree of control is to 75% or 100%:

| Knot Index | Degree of Control |
|---|---|
| 0.8 | 80% |
| 0.5 | 90% |
| 0.1–0.4 | 95–99% |

The results reported in Table II are the average of the knot index assigned to each test. Where two or more different formulations, or batches thereof, were employed the average knot index for each is reported. The compounds of this invention were highly effective against root-knot nematodes.

TABLE I

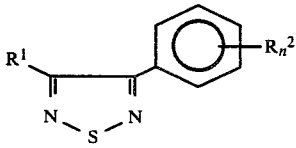

| Compd. No. | $R^1$ | $R^2$ | $MP^a$, $BP^b$, $NMR^c$ |
|---|---|---|---|
| 1 | Cl | H | 31.5–32.5 |
| 2 | " | 3-Cl | 40–41 |
| 3 | " | 4-Cl | 37–38.5 |
| 4 | " | 3-Br | 42–45 |
| 5 | " | 4-Br | 74–75.5 |
| 6 | " | 3-F | 68–69/0.02 mm |
| 7 | " | 4-F | 35–36.5 |
| 8 | " | 4-CN | 103.5–104 |
| 9 | " | 3-$CH_3$ | 2.40 (s, 3H) |
|   |   |   | 7.3–7.9 (m, 4H) |
| 10 | " | 4-$CH_3$ | 27–28 |
| 11 | " | 2-$OCH_3$ | 3.85 (s, 3H) |
|   |   |   | 6.95–7.70 (m, 4H) |
| 12 | " | 3-$OCH_3$ | 3.85 (s, 3H) |
|   |   |   | 6.95–7.70 (m, 4H) |
| 13 | " | 4-$OCH_3$ | 73–74 |
| 14 | " | 3-$OCHF_2$ | 6.60 (t, 1H) |
|   |   |   | 7.15–8.00 (m, 4H) |
| 15 | " | 4-$OCCH_3$ (O=) | 101.5–102.5 |
| 16 | " | 2-Cl, 4-Cl | 80/0.1 mm |

TABLE I-continued

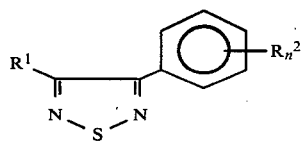

| Compd. No. | $R^1$ | $R^2$ | $MP^a$, $BP^b$, $NMR^c$ |
|---|---|---|---|
| 17 | " | 3-Cl, 4-Cl | 64–65.5 |
| 18 | F | H | 110/0.7 mm |
| 19 | " | 3-F | 37–38 |
| 20 | " | 3-$CH_3$ | 28.5–29 |
| 21 | F | 3-$OCH_3$ | 53–54 |
| 22 | $OCH_3$ | H | 4.15 (s, 3H) |
|   |   |   | 7.30–7.60 (m, 3H) |
|   |   |   | 8.00–8.30 (m, 2H) |
| 23 | " | 2-Cl | 58.5–60 |
| 24 | " | 3-Cl | 45–47 |
| 25 | " | 4-Cl | 71.5–72.5 |
| 26 | " | 4-Br | 80–83 |
| 27 | " | 2-F | 4.51 (s, 3H) |
|   |   |   | 7.00–7.90 (m, 4H) |
| 28 | " | 3-F | 35–40 |
| 29 | " | 4-F | 64–65 |
| 30 | " | 4-CN | 123–124.5 |
| 31 | " | 4-$CH_3$ | 2.40 (s, 3H) |
|   |   |   | 4.20 (s, 3H) |
|   |   |   | 7.30 (d, 2H) |
|   |   |   | 8.05 (d, 2H) |
| 32 | " | 4-$OCH_3$ | 69–69.5 |
| 33 | $OCHF_2$ | 4-Cl | 29–32 |
| 34 | $OCHF_2$ | 4-F | 39–42 |
| 35 | $OC_2H_5$ | H | 1.55 (t, 3H) |
|   |   |   | 4.60 (q, 2H) |
|   |   |   | 7.30–7.60 (m, 3H) |
|   |   |   | 8.00–8.30 (m, 2H) |
| 36 | $OCH_2CF_3$ | " | 42–44 |
| 37 | $OCH_2C=CH_2$ | " | 5.00–5.20 (m, 2H) |
|   |   |   | 5.20–5.70 (m, 2H) |
|   |   |   | 5.90–6.60 (m, 1H) |
|   |   |   | 7.20–7.60 (m, 2H) |
|   |   |   | 8.00–8.20 (m, 2H) |
| 38 | $OCH_2C\equiv CH$ | " | 46.5–48 |
| 39 | $OC_6H_5$ | " | 72–74 |
| 40 | $OC(=O)-N(CH_3)_2$ | " | 78–81 |
| 41 | $OC(=O)-N(CH_3)_2$ | 4-Br | 137–138 |
| 42 | $OC(=O)-N(CH_3)_2$ | 4-$CH_3$ | 91.5–92.5 |
| 43 | $SCH_3$ | H | 2.75 (s, 3H) |
|   |   |   | 7.40–7.70 (m, 4H) |
|   |   |   | 7.90–8.10 (m, 3H) |
| 44 | $SC(=O)N(CH_3)_2$ | 4-Cl | 153–154.5 |
| 45 | CN | H | 55–56 |

$^a$MP = Melting Point Range in ° centigrade.
$^b$BP = Boiling Point Range in ° centigrade at specified pressure (mm Hg)
$^c$NMR = ppm, $CDCl_3$

TABLE II

Nematicidal Activity of 4-Aryl-3-substituted-1,2,5-thiadiazoles
Soil Incorporated Evaluation of the Activity Against the Root-knot Nematode

| Cmpd. No. | Rate of Application (ppm) | Knot Index* Average[1] | Plant Injury[2] |
|---|---|---|---|
| 1 | 25.0 | 0.65 | 0 |
|   | 10.0 | 1.50 | 0 |
|   | 10.0 | 0.00 | 1 |
|   | 5.0 | 0.00 | 1[3] |
|   | 2.5 | 0.00 | 1[3] |
| 2 | 25.0 | 0.00 | 2 |
|   | 10.0 | 0.40 | 1 |
|   | 5.0 | 0.50 | 0 |
|   | 10.0 | 0.00 | 0[3] |
|   | 5.0 | 0.75 | 0 |
|   | 2.5 | 0.75 | 0 |
|   | 10.0 | 3.25 | 0 |
|   | 5.0 | 4.00 | 0 |
|   | 2.5 | 4.00 | 0 |
| 3 | 25.0 | 0.25 | 0 |
|   | 10.0 | 1.00 | 0 |
|   | 5.0 | 4.00 | 0 |
|   | 10.0 | 0.77 | 0 |
|   | 5.0 | 1.00 | 0[3] |
|   | 2.5 | 1.00 | 0[3] |
| 4 | 25.0 | 0.00 | 0 |
|   | 10.0 | 0.00 | 0 |
|   | 10.0 | 0.75 | 0 |
|   | 5.0 | 2.00 | 0 |
|   | 2.5 | 2.60 | 0 |
| 5 | 25.0 | 0.00 | 0 |
|   | 10.0 | 2.50 | 0 |
|   | 5.0 | 4.00 | 0 |
| 6 | 25.0 | 0.00 | 1 |
|   | 10.0 | 0.17 | 0 |
|   | 2.5 | 0.50 | 0[3] |
| 7 | 25.0 | 2.50 | 0[3] |
|   | 10.0 | 4.00 | 0 |
|   | 2.5 | 4.00 | 0[3] |
| 8 | 25.0 | 0.00 | 2 |
|   | 10.0 | 0.20 | 0[3] |
|   | 5.0 | 0.20 | 0 |
|   | 10.0 | 0.90 | 2[3] |
|   | 2.5 | 1.67 | 1 |
| 9 | 25.0 | 0.00 | 0 |
|   | 10.0 | 0.67 | 0 |
|   | 10.0 | 0.87 | 0 |
|   | 5.0 | 2.00 | 0 |
|   | 2.5 | 3.33 | 0 |
| 10 | 25.0 | 0.10 | 1 |
|   | 10.0 | 0.35 | 1 |
|   | 5.0 | 1.50 | 0 |
|   | 25.0 | 0.10 | 0 |
|   | 10.0 | 4.00 | 0 |
|   | 5.0 | 4.00 | 0 |
| 11 | 25.0 | 0.90 | 0 |
|   | 10.0 | 3.50 | 0 |
|   | 5.0 | 4.00 | 0 |
| 12 | 25.0 | 0.00 | 1 |
|   | 10.0 | 0.80 | 0 |
|   | 5.0 | 2.00 | 0 |
|   | 10.0 | 0.00 | 3 |
|   | 5.0 | 0.07 | 2 |
|   | 2.5 | 0.73 | 1 |
| 13 | 25.0 | 0.00 | 2 |
|   | 10.0 | 1.00 | 0 |
|   | 5.0 | 4.00 | 0 |
|   | 10.0 | 4.00 | 0 |
|   | 5.0 | 4.00 | 0 |
|   | 2.5 | 4.00 | 0 |
| 14 | 25.0 | 2.00 | 0 |
|   | 10.0 | 2.67 | 0 |
|   | 2.5 | 3.67 | 0 |
| 15 | 25.0 | 1.27 | 0 |
|   | 10.0 | 2.67 | 0 |
| 16 | 25.0 | 2.00 | 0 |
|   | 10.0 | 4.00 | 0 |
|   | 5.0 | 4.00 | 0 |
| 17 | 25.0 | 0.00 | 2 |
|   | 10.0 | 1.40 | 0 |
|   | 10.0 | 0.93 | 0 |
|   | 5.0 | 3.00 | 0[3] |
|   | 2.5 | 4.00 | 0 |
| 18 | 50.0 | 0.00 | 2 |
|   | 25.0 | 0.70 | 2 |
|   | 5.0 | 1.60 | 0 |
| 19 | 25.0 | 0.40 | 1[3] |
|   | 10.0 | 4.00 | 0[3] |
|   | 2.5 | 4.00 | 0 |
| 20 | 25.0 | 0.07 | 2 |
|   | 10.0 | 0.23 | 2 |
|   | 2.5 | 1.20 | 1 |
| 21 | 25.0 | 0.43 | 2 |
|   | 10.0 | 0.00 | 2 |
|   | 2.5 | 0.50 | 1 |
| 22 | 25.0 | 0.00 | 0 |
|   | 10.0 | 0.50 | 0 |
|   | 5.0 | 0.50 | 0 |
|   | 10.0 | 0.17 | 1 |
|   | 5.0 | 1.50 | 0[3] |
|   | 2.5 | 2.33 | 0 |
|   | 10.0 | 2.25 | 0 |
|   | 5.0 | 3.25 | 0 |
|   | 2.5 | 4.00 | 0 |
|   | 10.0 | 0.30 | 0 |
| 23 | 25.0 | 0.65 | 0 |
|   | 10.0 | 2.50 | 0 |
|   | 5.0 | 3.00 | 0 |
| 24 | 25.0 | 2.50 | 0 |
|   | 10.0 | 4.00 | 0 |
|   | 5.0 | 4.00 | 0 |
| 25 | 25.0 | 0.00 | 0 |
|   | 10.0 | 0.65 | 0 |
|   | 10.0 | 0.50 | 0 |
|   | 5.0 | 3.00 | 0 |
|   | 2.5 | 4.00 | 0 |
|   | 10.0 | 0.07 | 0 |
|   | 5.0 | 0.07 | 0 |
|   | 2.5 | 0.50 | 0[3] |
| 26 | 25.0 | 0.00 | 0 |
|   | 10.0 | 0.10 | 0 |
|   | 5.0 | 0.65 | 0 |
|   | 10.0 | 3.25 | 0 |
|   | 5.0 | 4.00 | 0 |
|   | 2.5 | 4.00 | 0 |
| 27 | 25.0 | 1.00 | 0 |
|   | 10.0 | 3.00 | 0 |
|   | 5.0 | 4.00 | 0 |
| 28 | 25.0 | 0.00 | 3 |
|   | 10.0 | 4.00 | 1 |
|   | 5.0 | 4.00 | 1 |
|   | 25.0 | 0.00 | 3 |
|   | 10.0 | 0.50 | 0 |
|   | 5.0 | 0.65 | 0 |
|   | 10.0 | 2.33 | 0 |
|   | 5.0 | 3.65 | 0 |
|   | 2.5 | 4.00 | 0[3] |
| 29 | 25.0 | 0.50 | 0 |
|   | 10.0 | 1.40 | 0 |
|   | 10.0 | 3.0 | 0 |
|   | 5.0 | 4.0 | 0 |
|   | 2.5 | 4.0 | 0 |
| 30 | 25.0 | 0.00 | 2 |
|   | 10.0 | 1.00 | 0 |
|   | 10.0 | 1.67 | 0 |
|   | 5.0 | 2.00 | 0 |
|   | 2.5 | 4.00 | 0 |
| 31 | 25.0 | 1.50 | 0 |
|   | 10.0 | 4.00 | 0 |
|   | 25.0 | 2.00 | 0 |
|   | 10.0 | 3.67 | 0 |
|   | 5.0 | 4.00 | 0 |
| 32 | 25.0 | 0.00 | 1 |

TABLE II-continued

Nematicidal Activity of 4-Aryl-3-substituted-
1,2,5-thiadiazoles
Soil Incorporated Evaluation of the Activity Against the
Root-knot Nematode

| Cmpd. No. | Rate of Application (ppm) | Knot Index* Average[1] | Plant Injury[2] |
|---|---|---|---|
|  | 10.0 | 0.90 | 0 |
|  | 5.0 | 3.50 | 0 |
|  | 10.0 | 4.00 | 0 |
|  | 5.0 | 4.00 | 0 |
|  | 2.5 | 4.00 | 0 |
|  | 10.0 | 1.50 | 0 |
|  | 5.0 | 2.00 | 0[3] |
|  | 2.5 | 4.00 | 0 |
| 33 | 25.0 | 0.90 | 2[3] |
|  | 10.0 | 2.50 | 0[3] |
|  | 2.5 | 4.00 | 0 |
| 34 | 25.0 | 1.50 | 1[3] |
|  | 10.0 | 3.00 | 0 |
|  | 2.5 | 4.00 | 0 |
| 35 | 25.0 | 0.00 | 3 |
|  | 10.0 | 2.50 | 0 |
|  | 5.0 | 4.00 | 0 |
| 36 | 25.0 | 2.50 | 0 |
|  | 10.0 | 4.00 | 0 |
|  | 5.0 | 4.00 | 0 |
| 37 | 25.0 | 0.50 | 0 |
|  | 10.0 | 2.00 | 0 |
|  | 5.0 | 1.67 | 0 |
| 38 | 25.0 | 1.00 | 0 |
|  | 10.0 | 2.50 | 0 |
| 39 | 25.0 | 1.00 | 0 |
|  | 10.0 | 2.00 | 0 |
|  | 5.0 | 3.50 | 0 |
|  | 10.0 | 1.33 | 0 |
|  | 5.0 | 3.00 | 0 |
|  | 2.5 | 4.00 | 0 |
| 40 | 50.0 | 0.00 | 4 |
|  | 25.0 | 0.00 | 4 |
|  | 5.0 | 0.60 | 3 |
| 41 | 50.0 | 0.27 | 3 |
|  | 25.0 | 1.27 | 2 |
|  | 5.0 | 2.67 | 0 |
| 42 | 50.0 | 0.27 | 3 |
|  | 25.0 | 1.27 | 2 |
|  | 5.0 | 2.00 | 0 |
| 43 | 25.0 | 0.00 | 2 |
|  | 10.0 | 0.35 | 0 |
|  | 10.0 | 0.43 | 3 |
|  | 5.0 | 1.50 | 2 |
|  | 2.5 | 4.00 | 2 |
| 44 | 25.0 | 1.00 | 0[3] |
|  | 10.0 | 2.00 | 0 |
|  | 10.0 | 2.67 | 2 |
|  | 5.0 | 4.00 | 0 |
|  | 2.5 | 4.00 | 0 |
| 45 | 25.0 | 0.67 | 0 |
|  | 10.0 | 1.33 | 0 |
|  | 2.5 | 2.67 | 0 |

*See test description for description of knot index
[1] Average of four replicates
[2] Plant Injury:
0 = no injury
1 = slight phytotoxicity
2 = moderate phytotoxicity
3 = severe phytotoxicity
4 = dead plant
[3] One or more of the plants died, unknown reasons. Knot Index and plant injury are based on remaining plants.

We claim:

1. A method for controlling nematodes which comprises applying to the soil in which plants are or are to be planted a nematicidal amount of a compound of the formula

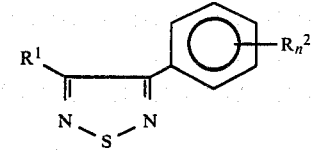

in which:
(a) $R^1$ is halogen, $R^2$ is halogen, cyano, methyl, methoxy, halomethoxy, or 4-methylcarbonyloxy, and n is 0 or 1; of $R^2$ is halogen and n is 2; or
(b) $R^1$ is methoxy, $R^2$ is halogen, cyano, 4-methyl or 4-methoxy, and n is 0 or 1; or
(c) $R^1$ is halomethoxy, $R^2$ is halogen, and n is 1; or
(d) $R^1$ is dimethylaminocarbonyloxy or dimethylaminocarbonylthio, $R^2$ is halogen or methyl, and n is 0 or 1; or
(e) $R^1$ is cyano, methylthio, 2-propenyloxy, 2-propynyloxy, 2,2,2-trifluoroethoxy, or phenoxy, and n is 0.

2. The method of claim 1 in which there is employed the compound in which n is 1, $R^1$ is chloro, and $R^2$ is 3-chloro or 3-methoxy or $R^1$ is methoxy and $R^2$ is 4-chloro.

3. A composition for controlling nematode damage in agricultural crops which comprises a nematode controlling amount of the compound of claim 1 in admixture with an agriculturally acceptable vehicle.

4. The composition of claim 3 containing the compound in which n is 1, $R^1$ is chloro, and $R^2$ is 3-chloro or 3-methoxy or $R^1$ is methoxy and $R^2$ is 4-chloro.

5. A compound of the formula

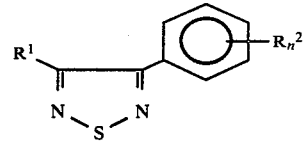

in which
(a) $R^1$ is halogen, $R^2$ is halogen, cyano, or methoxy, halomethoxy, or 4-methylcarbonyloxy, and n is 1; or $R^2$ is halogen and n is 2; or
(b) $R^1$ is methoxy, $R^2$ is halogen, cyano, or 4-methoxy and n is 1; or
(c) $R^1$ is halomethoxy, $R^2$ is halogen, and n is 1; or
(d) $R^1$ is dimethylaminocarbonyloxy or dimethylaminocarbonylthio, $R^2$ is halogen or methyl, and n is 0 or 1; or
(e) $R^1$ is cyano, methylthio, 2-propenyloxy, 2-propynyloxy, 2,2,2-trifluoroethoxy, or phenoxy, and n is 0.

6. The compound of claim 5 in which n is 1, $R^1$ is chloro, and $R^2$ is 3-chloro or 3-methoxy or $R^1$ is methoxy and $R^2$ is 4-chloro.

* * * * *